(12) United States Patent
Tamersoy et al.

(10) Patent No.: US 11,559,221 B2
(45) Date of Patent: Jan. 24, 2023

(54) MULTI-TASK PROGRESSIVE NETWORKS FOR PATIENT MODELING FOR MEDICAL SCANS

(71) Applicant: Siemens Healthcare GmbH, Erlangen (DE)

(72) Inventors: Birgi Tamersoy, Erlangen (DE); Vivek Kumar Singh, Princeton, NJ (US); Kai Ma, Princeton, NJ (US); Terrence Chen, Princeton, NJ (US); Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 970 days.

(21) Appl. No.: 16/361,553

(22) Filed: Mar. 22, 2019

(65) Prior Publication Data
US 2020/0297237 A1 Sep. 24, 2020

(51) Int. Cl.
*A61B 5/055* (2006.01)
*G16H 50/20* (2018.01)
*A61B 5/00* (2006.01)
*G06N 20/20* (2019.01)
*A61B 90/00* (2016.01)
*A61B 5/11* (2006.01)

(52) U.S. Cl.
CPC ............ *A61B 5/055* (2013.01); *A61B 5/0077* (2013.01); *A61B 5/1121* (2013.01); *A61B 5/7267* (2013.01); *A61B 90/39* (2016.02); *G06N 20/20* (2019.01); *G16H 50/20* (2018.01)

(58) Field of Classification Search
CPC ..... A61B 5/7267; A61B 5/0064; G16H 50/20
See application file for complete search history.

(56) References Cited

U.S. PATENT DOCUMENTS

| 2005/0267348 A1* | 12/2005 | Wollenweber | A61B 6/544 600/407 |
| 2015/0302594 A1* | 10/2015 | Moore | G06T 7/521 348/47 |
| 2016/0109545 A1* | 4/2016 | Forthmann | G06T 7/73 382/131 |
| 2018/0181802 A1* | 6/2018 | Chen | G06V 10/454 |

OTHER PUBLICATIONS

Kokkinos, Iasonas. "Ubernet: Training a universal convolutional neural network for low-, mid-, and high-level vision using diverse datasets and limited memory." Proceedings of the IEEE Conference on Computer Vision and Pattern Recognition. Sep. 2017. 1-19.
Rusu, Andrei A., et al. "Progressive neural networks." arXiv preprint arXiv:1606.04671 (2016).

* cited by examiner

*Primary Examiner* — Jason M Ip

(57) ABSTRACT

For training for and performance of patient modeling from surface data in a medical system, a progressive multi-task model is used. Different tasks for scanning are provided, such as landmark estimation and patient pose estimation. One or more features learned for one task are used as fixed or constant features in the other task. This progressive approach based on shared features increases efficiency while avoiding reductions in accuracy for any given task.

18 Claims, 4 Drawing Sheets

MULTI-TASK PROGRESSIVE NETWORKS FOR PATIENT MODELING FOR MEDICAL SCANS

BACKGROUND

The present embodiments relate to medical scanning. Medical scanning is performed for diagnosis and/or therapy in a clinical setting. The clinical setup may include patient modeling. The patient modeling for scanning includes, for example: localization of external body markers for determining scan ranges, estimation of patient pose for validating patient registration or positioning for the scan, estimation of patient body shape for determining patient ISO-center in computed tomography (CT) or estimating accurate Specific Absorption Rate (SAR) parameters in magnetic resonance (MR), estimation of patient weight and/or height for validating patient registration or setting intensity, and/or estimation of internal body markers for simulating topograms and/or CT images to guide scanning. Different clinical setups may use two or more tasks in the patient modeling.

When scanners are equipped with optical sensors, the optical sensor measurement may be used to solve for any of the patient modeling tasks. Where multiple tasks for patient modeling are used, a separate solution (i.e. model) may be applied for each task. These task-specific solutions are run in parallel or cascaded together depending on the nature of the problem. For example, the patient pose is first detected from the sensor measurement, then the external body markers are localized from the output pose and the input sensor measurement, and then the patient shape is estimated from the body markers and the original sensor measurement. On a totally separate execution flow, the height and the weight of the patient may be estimated as well. The fact that all these tasks rely on the same input (the sensor input) and are highly correlated is not leveraged in the separate-solution approach. Furthermore, when separate models are cascaded together in an execution flow, errors from the earlier stages are propagated to the later stages.

SUMMARY

Systems, methods, and instructions on computer readable media are provided for training for and performance of patient modeling from surface data in a medical system. A progressive multi-task model is used. Different tasks for scanning are provided, such as landmark estimation and patient pose estimation. One or more features learned for one task are used as fixed or constant features in the other task. This progressive approach based on shared features increases efficiency while avoiding reductions in accuracy for any given task.

In a first aspect, a method is provided for patient modeling from surface data in a medical system. A sensor captures an outer surface of a patient. The surface data is from the capturing of the outer surface of the patient. A first value of a first patient characteristic is estimated from the surface data as a first task. The first patient characteristic is estimated by a first machine-learned model of a progressive multi-task network. A second value of a second patient characteristics is estimated from the surface data as a second task. The second patient characteristic is estimated by a second machine-learned model of the progressive multi-task network. The second machine-learned model includes features learned in training the first machine-learned model where the second machine-learned model was trained after the first machine-learned model using the features learned in training the first machine-learned model as fixed in the training of the second machine-learned model. Scanning of the patient is controlled based on the first and second values of the first and second patient characteristics.

In some embodiments, the capturing is by a depth sensor, such as a camera where the surface data is based on optical measurements. The surface data represents an outer surface (e.g., skin and/or clothing) of a patient, such as while the patient is on a bed of a medical scanner.

The first characteristic may be a same or a different type of characteristic than the second characteristic. The characteristics are characteristics of the patient, such as locations of particular parts of the patient while resting on the bed and/or other descriptors or properties of the patient. In some embodiments, the characteristics are one of two or more from the group of landmarks (e.g., top of head and/or shoulder, or locations of specific joints), pose (e.g., facing up, on side, or facing down), body shape (e.g., mesh representing the outer surface in two or three dimensions), weight, height, or internal body markers (e.g., estimate of location of specific organs).

The features shared from the first machine-learned model in the second machine-learned model are learned features from machine training. The machine training determines a value of a weight, a connection, a convolution kernel, or other extraction of information as a variable or parameter learned in machine training. For a progressive model, the second machine-learned model was trained using at least some of the features learned in training the first machine-learned model as constants such that the features do not change in the training for estimating by the first or second machine-learned model.

In one embodiment, the shared features are learned convolution kernels from within the first machine-learned model. The machine-learned models are classifiers, estimators, predictors, or networks learned by machine training from training data including many input samples and corresponding ground truth outputs for the samples. The machine-learned model is, for example, a neural network. In one embodiment, at least the first machine-learned model is a first image-to-image network, such as an encoder and decoder formed as a fully convolutional neural network. The second machine-learned model may be another image-to-image network where the features from an encoder of the first image-to-image network are used in an encoder of the second image-to-image network. In another embodiment, the second machine-learned model is a neural network where the features are from a bottleneck of the first image-to-image network and are used as inputs to the neural network.

In another embodiment, the first machine-learned model is a first encoder-decoder trained to output upper body landmarks as the first characteristic. The second machine-learned model is a second encoder-decoder trained to output lower body landmarks as the second characteristic. A third value for a third characteristic is estimated as a third task by a third machine-learned model. The third machine-learned model was trained after the first machine-learned model using the features learned in training the first or first and second machine-learned models as fixed in the training of the third machine-learned model.

The control is by configuring a medical diagnostic imaging scanner or therapeutic scanner to scan based on the first and second values. Various embodiments for control are possible. The second characteristic may be body shape. The scanner is controlled by setting an iso-center using the body shape. The first characteristic may be one or more landmarks. The scanner is controlled by setting a scan range using the one or more landmarks. The second characteristic may a patient pose. The scanner is controlled by re-orienting (e.g., inputting a correct pose into the scanner) the patient on a bed. The second characteristic may be body shape. The scanner is controlled by performing magnetic resonance scan with specific absorption rate settings based on the body shape. The second characteristic may be a patient weight, height, or weight and height. The scanner is controlled by configuring a scan based on the weight, height, or weight and height. The second characteristic may be an internal body marker. The scanner is controlled by controlling based on a simulated topogram or image from the internal body marker.

In a second aspect, a medical scanner system uses patient modeling. A depth camera is configured to measure depths to a patient while the patient is on a patient bed in a medical scanner. An image processor is configured to determine two or more of patient pose, patient height, patient weight, patient shape, and patient landmark by application of a progressive multi-task machine-learned model. A controller is configured to operate the medical scanner based on the patient pose, patient height, patient weight, and patient landmark. In one embodiment, the progressive multi-task machine-learned model is a neural network for each of the two or more of the patient pose, patient height, patient weight, and patient landmark, and features learned from one of the neural networks are used in another one of the neural networks.

In a third aspect, a method is provided for machine training a progressive multi-task model for patient scanning. A first neural network is machine trained to output one or more landmarks on a patient from a camera image. The machine training of the first neural network trains first features of the first neural network. At least one of the first features are assigned to a second neural network. The second neural network is trained to output patient pose or patient weight from the camera image. The machine training of the second neural network uses the at least one of the first features of the first neural network as fixed during the machine training of the second neural network. The first and second neural networks are stored as a machine-learned progressive multi-task machine-learned model. In one embodiment, the first neural network is machine trained as an encoder-decoder architecture. The second neural network is machine trained with the first features being from an encoder of the encoder-decoder architecture.

Any one or more of the aspects described above may be used alone or in combination. Any aspects of one of method, system, or computer readable media may be used in the others of method, system, or computer readable media. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Figure 1:
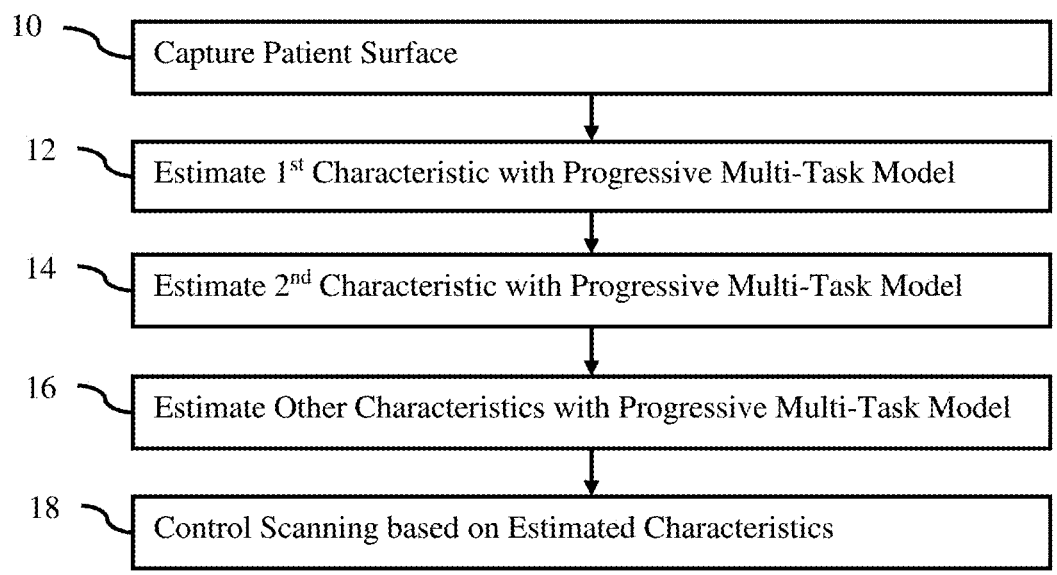
FIG. 1 is a flow chart diagram of one embodiment of a method for patient modeling from surface data in a medical system.

A multi-task progressive network solves for multiple patient modeling problems as the multiple tasks. One network interconnected by features progressively trained for different tasks provides for efficient and accurate solution of the multiple patient modeling tasks. One part of the network is trained for one task, and then another part of the network is trained for the other task. This progressive training uses one or more features learned for the first or earlier task as constant (i.e., not trainable) features in the part of the network trained for the second or later task.

In patient modeling, this progressive multi-task network does not require additional activations after lateral connections (i.e., features from earlier trained network are used as constants, avoiding training those features for use in the later trained network), lateral connections may not be included in any decoding stages (i.e., features from a decoder are not used in the other network for other tasks), totally different network architectures may be used for different tasks, and any task may be divided into sub-tasks (e.g., dividing landmark detection into detection of upper body landmarks and lower body landmark tasks to create sub-tasks depending on the requirements). These (activations, lateral connections in decoding, etc.) are not used in one embodiment, but may be used in other embodiments.

The multi-task progressive machine-learned network may increase efficiency as compared to training separate networks for each task. Since all tasks share some (e.g., a significant amount of computation in the form of the same features), the inference of this method may be faster than having separate solutions for each task and running them in sequence and/or in parallel. Since the consequent columns or task-specific parts of the network are supported by the features of the previous columns (e.g. lateral connections of features between the upper and lower body sub-task networks), the later columns may be made much simpler than if trained separately. In other words, the model complexity may be reduced for all subsequent tasks. Solving for new relevant tasks (e.g. localization of arm landmarks) may be done without the requirement of re-training for the previous tasks. This makes adding new tasks to the solution framework more efficient and risk free.

The multi-task progressive machine-learned network may increase performance as compared to training separate networks for each task. Since each task is optimized separately in progressive training, the best possible accuracy for that given task may be reached without reduction in accuracy of other tasks. Since the model is trained progressively, the performances of the previously learned solutions do not change. The marker localization task is traditionally addressed in similar image-in, image-out setups. Where the multi-task progressive network solution groups the body markers in two categories as separate tasks (e.g., progressively trained sub-tasks), the required model complexity may be controlled for different product requirements for these two groups explicitly.

The multi-task progressive machine-learned network may increase flexibility. Customized execution flows may be provided since the framework inherently provides mechanisms to generate workflow specific "task graphs." The multi-task progressive network architecture is customized to include networks for tasks specific to the workflow. One example is: for a routine CT scan, the workflow and sequence of patient modeling tasks are upper body marker localization, lower body marker localization, patient pose estimation, and patient height and/or weight estimation. Another example is: for a trauma CT scan (where lower-body is heavily occluded), the workflow and sequence of patient modeling tasks are upper body marker localization and patient pose estimation. Yet another example is: for a standing X-ray scan, the workflow and sequence of patient modeling tasks are upper body marker localization, lower body marker localization, arm body marker localization, and patient height and/or weight estimation.

As a result of efficiency, performance, and/or flexibility, more accurate results are provided using less computational power and less memory resources.

FIG. 1 is a flow chart diagram of one embodiment of a method for patient modeling from surface data in a medical system. A machine-learned network includes sub-parts separately and sequentially trained for different tasks. One or more features from one or more sub-parts are progressively used as fixed features in one or more other sub-parts. In application, the values for these features from one sub-part are progressively used as values for the same features in the one or more other sub-parts.

Figure 6:
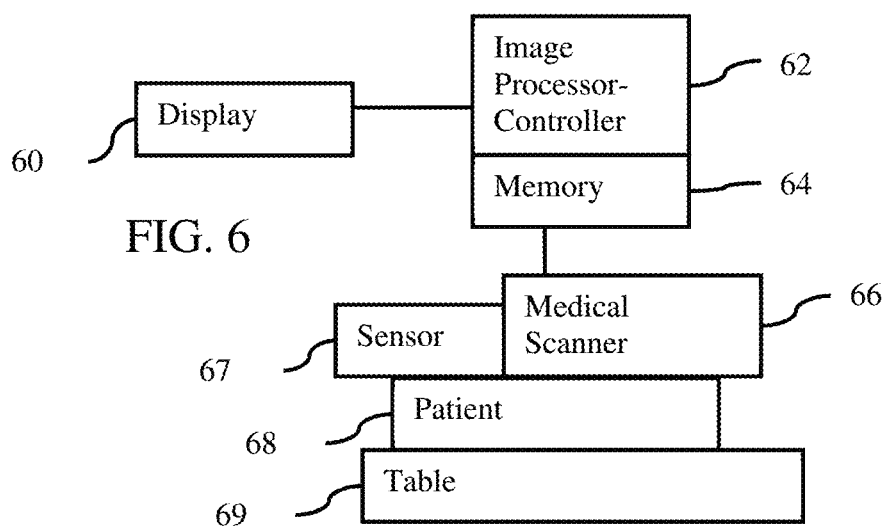
FIG. 6 is a block diagram of one embodiment of a medical scanner system using patient modeling.

The method of FIG. 1 is performed by the medical scanner system of FIG. 6 or another system. For example, the sensor, such as a depth camera, captures the patient surface. An image processor estimates the values for two or more patient characteristics. A controller, such as the image processor, controls scanning by a medical scanner based on the values of the estimated characteristics. Other devices may be used to perform any of the acts. In other embodiments, a server, workstation, or computer performs the method without acts 10 and/or 18.

The method is performed in the order shown (e.g., top to bottom or numerical), but other orders may be used. For example, acts 12, 14, and 16 may be performed simultaneously or in reverse order depending on any sharing of features in progression. One estimation is performed before another due to progression. In other embodiments, all characteristics may be computed in parallel since only low-level features are shared.

Additional, different or fewer acts may be provided. For example, act 18 is not provided. As another example, acts for configuring other aspects of the scanning are performed based on user input or other information. In yet another example, acts for positioning the patient and/or activating scanning of the patient are included.

In act 10, a sensor captures an outer surface of a patient. The sensor is a depth sensor (e.g., depth camera), such as a 2.5D or RGBD sensor (e.g., Microsoft Kinect 2 or ASUS Xtion Pro). The depth sensor may directly measure depths, such as using time-of-flight, interferometry, or coded aperture. The depth sensor may be a camera or cameras capturing a grid projected onto the patient. The sensor may be multiple cameras capturing 2D images from different directions, allowing reconstruction of the outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient viewed from one side from head to toe and hand to hand or just the torso. The sensor captures the outer surface with the patient in a particular position and pose, such as capturing a front facing surface as the patient lies in a bed or on a table for treatment or imaging.

The outer surface is the skin of the patient. In other embodiments, the outer surface includes clothing. The sensor may use a frequency that passes through clothing and detects skin surface. Alternatively, the outer surface is the clothing.

Figure 2:
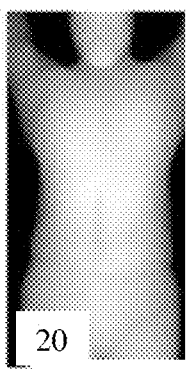
FIG. 2 is an example depth image.

The outer surface is captured as depths from the sensor to different locations on the patient, an image or photograph of the outside of the patient, or both. The sensor outputs the sensed image and/or depths. The measurements of the outer surface from the sensor are surface data for the patient. FIG. 2 shows an example image 20 from surface data where the intensity in grayscale is mapped to the sensed depth. Alternatively, the sensor measurements are processed to determine the outer surface information, such as stereoscopically determining the outer surface from camera images from different angles with image processing or using image streams and performing structure-from-motion.

In one embodiment, the surface data may include different representations of the patient. Two or more channels are created. For example, two images have pixel intensity modulated by the amplitude of the information for the channel (e.g., one by depth and the other by color). In one embodiment, given a 3D surface of the patient's body (skin surface), 2D projections of this data—skin surface image (e.g., height of the surface from the scanner table at each location in the image) and depth image (e.g., measure the thickness of the person at each location in the image)—are formed by image processing from the output of the sensor. Each channel provides different information. One channel provides a distance or height of front surface locations to a bed or table on which the patient lies, to the sensor, and/or relative to another location. The outer surface as sensed and the known location of the sensor to the bed are used to determine the distance. Another channel is a thickness of the patient. The thickness may be a difference of a given depth from the maximum and minimum depth. Other thickness may be used. The first channel stores the depth of the body surface as observed from the front or looking at the patient resting on the patient bed, and second channel stores the thickness computed by measuring the distance between the closest and furthest point as observed from the front. Other channels may be used, such as one channel for depth from the sensor and another channel for optical image of the patient. Other surface data may be used.

The surface data is used at the resolution of the sensor. For example, the surface data is at 256×256 pixels. Other sizes may be used, including rectangular fields of view. The surface data may be filtered and/or processed. For example, the surface data is altered to a given resolution. As another example, the surface data is down sampled, such as reducing 256×256 to 64×64 pixels. Each pixel may represent any area, such as each pixel as down sampled to 64×64 representing 1 $cm^2$ or greater. Alternatively, the sensor captures at this lower resolution. The surface data may be cropped, such as limiting the field of view. Both cropping and down sampling may be used together, such as to create 64×64 channel data from 256×312 or other input channel data. Greater or lower resolution may assist in regression.

In another approach, the surface data is normalized prior to input. The surface data is rescaled, resized, warped, or shifted (e.g., interpolation). The surface data may be filtered, such as low pass filtered. The surface data (e.g., depth images) with or without further processing is input for estimation of multiple patient characteristics in patient modeling.

In act 12, an image processor estimates a first value of a first patient characteristic from the surface data as a first task. In the patient modeling, the outer surface data is used for multiple tasks, such as tasks to estimate different characteristics of the patient. For example, a volume or weight of the patient (e.g., value of 120 pounds is estimated for the weight characteristic) is estimated as one task.

The image processor estimates the characteristic by input of the surface data into a machine-learned model. The machine-learned model is any machine-learned classifier or network. For example, a neural network is used to regress the relationship between the input surface data and the output characteristic. A fully connected neural network, convolutional neural network, fully convolutional network, dense net, or another neural network may be used. In one embodiment, an image-to-image network (e.g., U-net) is used, such as an encoder-decoder network where the encoder increases abstraction and decreases resolution, providing values for bottleneck features to the decoder for decreasing abstraction and increasing resolution. A support vector machine, clustering based machine learning, Bayesian, or other machine-learned regressor may be used.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning. Training data, including many samples of the input surface data and the corresponding ground truths (i.e., value of the characteristic), is used to train. The relationship of the input to the output is machine learned. Once trained, the machine-learned model (machine-learned network) may be applied to estimate the characteristic from input surface data for a patient.

Any characteristics of the patient may be estimated. The characteristic is a descriptor of the patient or other indicator of a property of the patient. Different patients may have the same or different values of the characteristic.

The characteristic may be pose. The pose may be in any of various classes, such as three categories for laying on back, laying on front, and laying on side. In other examples, the pose includes four classes as head-first supine, feet-first supine, head-first prone, and feet-first prone. Additional classes may be provided for pose, such as indicating relative position of arms, legs, and/or head to the torso.

The characteristic may be body shape. The body shape is a three-dimensional surface, such as a fit mesh, or other representation of the shape of the body. The entire body or part of the body may be represented in the body shape characteristic, such as a mesh representing the outer surface of the patient as viewed from a given direction or a mesh representing just the torso.

The characteristic may be weight and/or height. The characteristic may be internal body markers. Locations of landmarks within the body may be estimated, such as estimating the location of particular organs or parts of organs or estimating the location of skeletal structures.

In one embodiment, the characteristic is a location of one or more exterior landmarks. The landmarks are anatomical points or regions. For example, landmarks may include the nose, eyes, neck, sternum, fingers, hands, or any other part of the patient represented in the surface data. In one embodiment, the landmarks are a top of the head, a bottom of the head, shoulder top, shoulder bottom, torso bottom, torso top, groin, knee bottom, knee top, ankle bottom, and ankle top where top and bottom are in reference to anatomy and/or the bed.

Figure 3:
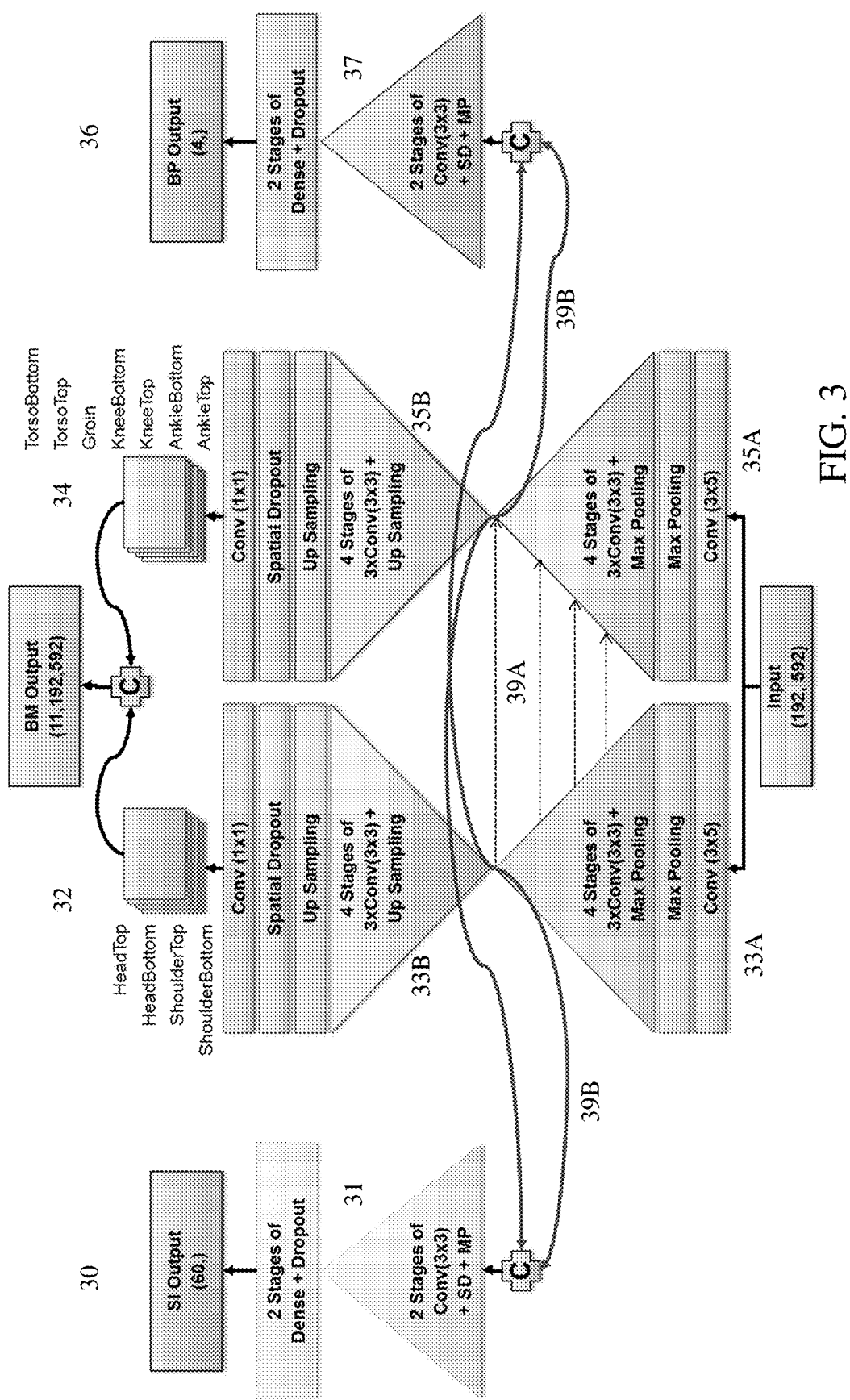
FIG. 3 shows an example progressive multi-task network architecture.

FIG. 3 shows an example image-to-image neural network 32 formed from an encoder 33A and decoder 33B for estimating the locations of four landmarks. Additional, different, or fewer landmark locations may be estimated. The landmarks are the head top, head bottom, shoulder top, and shoulder bottom, but other landmarks may be used. The image-to-image neural network 32 is trained to output a four channel heatmap or four heatmaps. At the input resolution or a different resolution, a probability of each pixel or voxel being a given landmark is provided as the heatmap for a channel.

The encoder 33A of the image-to-image network 32 of FIG. 3 includes a convolution layer with a 3×5 kernel for receiving the input 192x529 surface data. The convolution layer is followed by a max pooling layer. The output of the max pooling layer is provided to four stages of increasing abstraction and decreasing resolution. Each stage has three convolution layers followed by a max pooling layer. Each convolution layer has 12 convolutions or kernels with 3×3 kernel size. The final stage outputs values of bottleneck features to the decoder 33B. The decoder 33B includes four stages each having three convolution layers followed by an up-sampling layer. The convolution layers of the encoder 33B have the same or different structure as the encoder 33A. The final stage of the decoder 33B outputs to an up-sampling layer, which outputs to a spatial dropout layer. A final convolution layer with 1×1 kernel size outputs the estimated locations of the landmarks. The network architecture may have 32 k parameters that are learned through machine training. Other architectures may be used. Different numbers of stages, layers, parameters, and/or convolutions in a layer may be used. Additional or different kernel sizes, combinations of layers, types of layers, input resolution, and/or output resolution may be used.

Referring again to FIG. 1, the image processor estimates a value of another characteristic from the surface data as a second task in act 14. Different networks or sub-parts of a network are used to estimate for other characteristics. The estimate is for a different task.

The characteristic may be any one of external landmarks, pose, body shape, weight, height, or internal body markers. In one embodiment, the different task is estimation of a different type of characteristic. A different one of external landmark, pose, body shape, weight, height, or internal body marker are estimated than the first characteristic. For example in FIG. 3, the image-to-image network 32 estimates the locations of four external landmarks. The neural network 30 and the neural network 36 estimate the different characteristics of body shape and body pose, respectively. In other embodiments, the second characteristic is of a same type as the first characteristic, but of different characteristics. For example, different landmarks are located by the different estimates and corresponding networks. In the example of FIG. 3, the image-to-image network 32 estimates locations of upper body landmarks as first characteristics, and the image-to-image network 34 estimates the locations of lower body landmarks (e.g., torso bottom, torso top, groin, knee bottom, knee top, ankle bottom, and ankle top) as second characteristics.

A different machine-learned model than the model used for estimating the first characteristic is used for the task of estimating the second characteristic. The same or different type of machine-learned model discussed above may be used. For the same type, the same or different architecture (e.g., number of layers, number of convolutions per layer, types of layers, order of layers, or other variations) may be used. In the example of FIG. 3, the second machine-learned network is an image-to-image network 34 (i.e., same type as the image-to-image network 32). An encoder 35A and decoder 35B form the image-to-image network 34. The image-to-image network 34 has a same layer arrangement and kernel size as the image-to-image network 32 but includes 15 filters per convolution layer instead of 12 of the image-to-image network 32, resulting in over 50 k parameters. The output is a 7 channel heatmap output instead of a 4 channel heatmap output. The upper and lower landmarks may be combined as an 11 channel heatmap output at the resolution (e.g., 192×592) of the input surface data.

Figure 5:
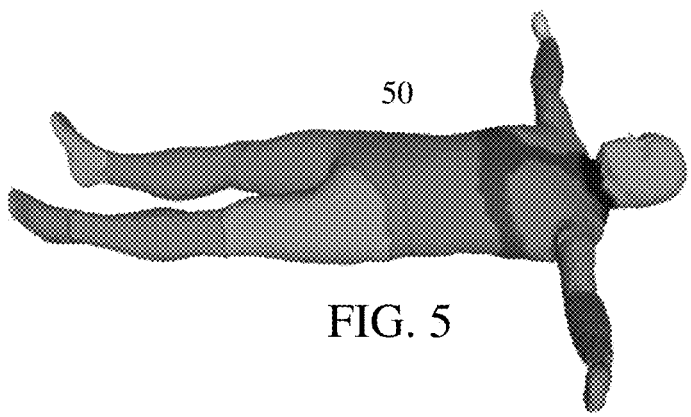
FIG. 5 illustrates an example estimated patient body shape characteristic.

The neural networks 30 and 36 are of different types than the image-to-image networks 32, 34. The body shape network 30 is designed or configured to output a 60-dimensional vector that represents a particular point in a pre-learned shape space. The values of the vector define the shape, such as based on a linear shape space using eigen vectors. FIG. 5 shows an example mesh 50 parameterized in the shape space. A dense net, sequential layer structure (e.g., feed forward without skip connections), convolutional neural network, or another network 31 is provided. In the example of FIG. 3, two stages of a convolution layer with 3×3 kernels, spatial dropout layer, and max pooling layer feed to two stages of dense layer and spatial drop out layer.

The body pose network 36 is designed or configured to output a class membership for pose, such as one of four classes (e.g., head-first supine, feet-first supine, head-first prone, and feet-first prone). A dense net, sequential layer structure (e.g., feed forward without skip connections), convolutional neural network, or another network 37 is provided. In the example of FIG. 3, two stages of a convolution layer with 3×3 kernels, spatial dropout layer, and max pooling layer feed to two stages of dense layer and spatial drop out layer.

Additional, different, or fewer networks 30, 32, 34, 36 may be provided in the multi-task progressive neural network. FIG. 3 shows four sub-parts where each sub-part handles a different patient modeling task. Other workflows may use two, three, five, or more patient modeling tasks and corresponding networks. The multi-task progressive neural network is designed or configured based on the number of tasks with each component network architecture being designed or configured based on the task. In FIG. 3, each of the columns, when examined separately, forms a Convolutional Neural Network (CNN).

The machine-learned models of the progressive multi-task network estimates the characteristics. The progressive multi-task network is a machine-learned network for performing multiple tasks. Each machine-learned model includes learned features, such as learned convolution kernels, for the task.

Rather than operating the networks 30, 32, 34, 36 independently, the networks for the tasks are related through shared features formed by progressive training. The training progresses through a sequence of the networks 30, 34, 32, 36, which allows subsequent training to use information from previous training of another one of the networks 30, 34, 32, 36. One or more features from one or more networks are used as features in a subsequent network. While training for a task, the shared components of that task from another previously trained network are frozen (i.e. kept constant), hence the performance of the previously learned tasks do not change. The resulting trained multi-task network is a progressive multi-task network as one or more parts use values for features from a previously applied part.

Figure 4:
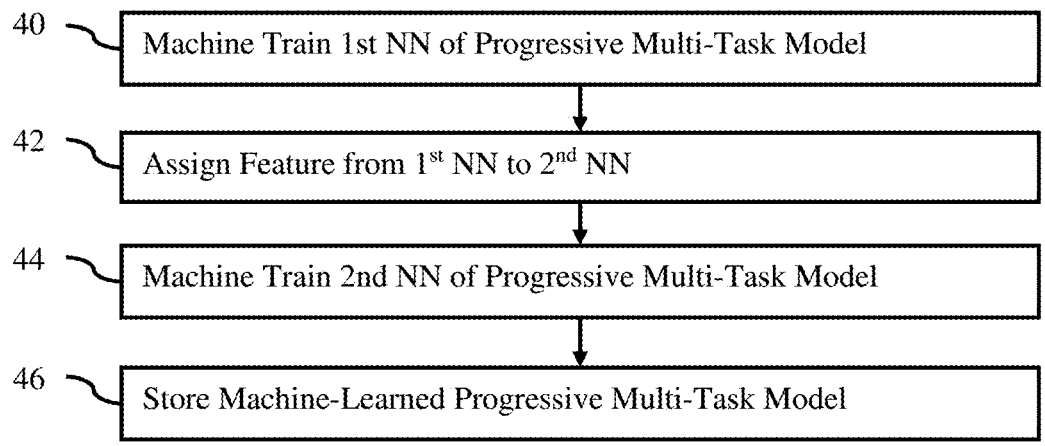
FIG. 4 is a flow chart diagram of one embodiment of a method for machine training a progressive multi-task model for patient scanning.

FIG. 4 is a flow chart diagram of one embodiment of a method for machine training a progressive multi-task model for patient scanning. One or more features learned for one task are used as constant, fixed, or set features (i.e., do not change the kernel values) in training and application in another task.

The training is performed by an image processor using training data (e.g., surface data samples and corresponding ground truth values for characteristics) stored in a database. Other devices may be used.

The acts are performed in the order shown or other orders. Additional, different, or fewer acts may be provided. For example, acts for training additional neural networks may be provided.

In act 40, the processor machine trains the neural network. The training learns weights, connections, filter kernels, and/or other parameters of a defined architecture. The weights, connections, filter kernels, and/or other parameters are the features being learned. For example, each of the convolution kernels in the network 32 are features being trained. Using the training data, the values of the parameters are adjusted and tested to determine the feature values leading to an optimum estimation of the output given an input sample. Adam or another optimization is used to train.

The neural network being trained is for one of the multiple tasks. For example, the image-to-image or encoder-decoder neural network 32 of FIG. 3 is first trained. The training optimizes the neural network 32 for the task, such as estimation of location of upper body external landmarks. The neural network 32 is trained to estimate a value for a characteristic from a camera image.

In act 42, one or more of the learned features are assigned to another one of the neural networks. For example, convolution kernels from each convolution layer and/or stage learned in training the image-to-image network 32 for the upper body landmark task are assigned to the corresponding convolution layers or stages for the image-to-image network 34 for the lower body landmark task.

Any sub-set or all the features from all or part of the initially learned neural network 32 are assigned to the other network. In the example of FIG. 3, the convolution features learned for the network 32 in each stage of the encoder 33B are assigned to the corresponding stages of the encoder 35B of the network 34. This assignment is represented by the links or lateral connections 39A (dashed horizonal lines). Since the convolution layers of the stages of the encoder 35B have additional convolutions, some of the convolutions in the encoder 35B are the features as learned for the network 32 and others are to be learned.

FIG. 3 shows other examples. The networks 30 and 36 are trained after the two image-to-image networks 32, 34. The features outputting the bottleneck values are assigned to the input of the networks 30, 36. This assignment is represented by the links 39B. The features of the encoders 33A and 35A are used to determine values used by the networks 31, 37. In alternative embodiments, different combinations of features are used for the different networks.

The progression of sequential training allows for assignment of features from previously trained networks to a network to be trained. These assigned features are fixed or not changed in training the subsequent network so that the estimation for the previously trained network maintains an accuracy. The assigned features, as constants, are used as part of training the free or trainable features of the subsequent network or networks.

In act 44, the processor machine trains the subsequent neural network to output values for one or more other characteristics. The same or different machine training, training data, and/or corresponding optimization is used. The defined network architecture is trained to estimate for the assigned task given the input samples and the fixed feature or features.

In the example of FIG. 3, the image-to-image network 34 is trained to estimate locations of lower body landmarks. The body shape network 30 is trained to estimate the body shape. The body pose network 36 is trained to estimate the body pose. Each network is trained to optimize the estimation for the corresponding task. The input for each network is the same—samples of surface data.

In training each subsequent network, one or more features from one or more previous networks are used. These assigned features are kept fixed or not changed in the training after having been trained for one network. The machine training of the subsequent neural network uses one or more features of the previously trained neural network as fixed during the machine training of the subsequent neural network. Other parameters of the subsequent networks are varied to train.

In FIG. 3, all four tasks share the heavy computational sections: the two encoders 33A and 35A. The training of the complete model is done progressively, in the order of task importance and/or difficulty given the requirements. In this setup, first the upper body marker network 32 is trained. Then, using some of the learned features (through lateral connections 39A), the lower body marker network 34 is trained. This is followed by the training of the body pose network 36 and shape initialization network 30. While training for a task, all the shared components of that task which were previously trained are frozen (i.e. kept constant), hence the performance of the previously learned tasks do not change. The networks 30 and 36 share the entire encoders 33A and 35A of the networks 32 and 34. The network 34 shares features from the convolution layers of the stages of the encoder 33A but also includes convolutions to be learned while also including the fixed, shared features.

FIG. 3 shows only four patient modeling tasks, but other and/or different tasks may be incorporated into this framework. The incorporation uses assigned features form prior trained networks by branching out at appropriate locations in the architecture using the previously learned features and training progressively. For example, tasks for localization of arm landmarks, estimation of internal landmarks, estimation of patient height, and/or estimation of patient weight and corresponding networks are used.

The progressive training is different than multi-task learning. In multi-task learning, a single network is defined that includes multiple outputs. An aggregated objective is used for the multiple outputs in the training, so that the error in each task influences all the tasks. The training tries to perform each task at the same time, optimizing for the joint objective. This optimization is difficult due to the joint objective. The accuracy of each individual task may be less due to solving for all tasks together. Dis-joint objectives that are optimized in turn for the single network may be used. This approach may lead to "catastrophic forgetting." When the current task is being optimized, the shared components of the solution model are altered. This hinders the performance on the tasks which were already optimized. By using fixed features assigned from a previously trained network, catastrophic forgetting may be avoided. The progressive training maximizes the accuracy for each task without reducing accuracy due to training for multiple tasks. Instead, the multi-task progressive network benefits from the similarity of the tasks and use of the same input without having a reduction in accuracy for any task.

After training the various networks, the trained networks are stored in act 46. The weights, connections, kernels, and/or other features learned for each network are stored. The progressive multi-task machine-learned network or model is stored.

The stored model may be used or applied. Copies of the stored model may be used or applied by different servers, image processors, computers, or workstations. In application, the values for the features of each network are determined based on input surface data for a patient. Where the same feature is provided in a network for a different task, the calculated value for that feature may be used without re-calculating since the features were fixed in the training. This increases efficiency in estimation of the characteristics.

Referring again to FIG. 1, the estimation of the value or values for the second characteristic uses the machine-learned model that was trained after another machine-learned model. Due to the progressive network, the features learned in training the earlier machine-learned model are used as fixed in the training and application of the subsequent machine-learned model. One or more features from one network are used as constants in another network where the constant features do not change during the training of the other network.

In act 16, the processor estimates a value or values for one or more other characteristics as one or more other tasks. One or more other machine-learned models are used to estimate. The machine-learned models are part of the progressive multi-task machine-learned network. These other machine-learned models were trained after one or more other machine-learned models, so include or may include one or more features from the earlier trained machine-learned models. The values calculated for these features for application of the earlier trained models are used in the other model. Since the features are the same and the values for the features are based on the same input, the already calculated values from application of one machine-learned model are used in application of the other machine-learned model. Alternatively, the feature is the same but relies on values of non-shared features, so the value is calculated for the subsequent machine-learned model.

In act 18, a controller controls scanning of the patient. The controller may be the image processor or a separate processor of the medical scanner. The scanning being controlled may be for therapy, such as application of X-rays or other radiation for treatment. The scanning being controlled may be for diagnosis, such as CT, MR, ultrasound, or another medical diagnostic imaging scanning. The control is by configuring the therapeutic or diagnostic scanner. The control may be for front-end control, such as intensity of transmission, region scanning, spacing or resolution of the scan, pattern of the scan, range of motion or spatial extent of the scan, scan sequence, and/or other scan setting. The control may be for back-end control, such as control of the type of filtering, the image process or processes applied, the format or what information is displayed, or other post acquisition or measurement operation.

The controller configures the medical scanner (e.g., computed tomography, fluoroscopy, or x-ray) based on one or more characteristics. The medical scanner may configure itself or at least part of the configuration is based on the values for the characteristics. The controller may configure by direct control the medical scanner. Alternatively, the user manually configures the medical scanner based on the values of the characteristics. Recommended settings may be output to the user based on the values of the characteristics.

One or more settings for imaging or scanning the patient may be adjusted or set using, at least in part, the values of the characteristics. The values may assist in planning a medical scan, such as defining a field of view and/or x-ray intensity to control dose from radiation. For CT scanning, the values may be used to determine the scan range. This may reduce the amount of ionizing radiation applied to the patient. The values may assist in scan sequence, coil placement, and/or scan position for magnetic resonance (MR) scanning. For ultrasound scanning, the values may assist in imaging frequency where a lower frequency is used for heavier patients. For fluoroscopy using dyna-CT scans, the values may be useful for positioning the patient and/or the scanner and controlling the x-ray source. Any setting or parameter of the medical scanner may be determined or configured based on the values.

The scanning is controlled based on the values for two or more characteristics. The different tasks in the patient modeling contribute to control of the scanning. The two or more values for the corresponding two or more characteristics are used together to control setting of one parameter of the scanner. Alternatively, different values and corresponding characteristics are used to set different parameters of the scanner.

In one embodiment, the body shape is used to control the iso-center. A gantry position and/or spatial position of the scan is oriented or located around an iso-center of the patient. Alternatively or additionally, the body shape is used to estimate the specific absorption rate (SAR). Rather than using a more simplistic model, the SAR for MR scanning may be set based on the patient model of the body shape. The distribution of density in the patient may be better modeled using the 3D mesh of the body shape.

In another embodiment, one or more landmarks are used to control a scan range. The start and/or stop position of the gantry and/or bed, the scan field of view, scan pattern, and/or scan density may be set based on the landmarks, such as scanning from an upper torso to a lower torso where the landmarks indicate the position of the torso of the patient. Landmarks may be used to provide a greater density or resolution for one region of the patient as compared to another region. Landmarks may be used to control various aspects of the spatial distribution of the scanning and/or for image processing scan data.

In yet another embodiment, the patient pose is used to control an output of a display or speaker. For example, the patient is to be posed in a particular way. If posed differently, then a display (e.g., projection or monitor display) and/or speaker indicates that the patient pose should be changed (i.e., re-orient the patient on the bed). Alternatively, the pose of the patient is changed in the scanner to reflect the actual pose of the patient. As another example, scanning is prevented unless the patient pose indicates proper positioning of the patient for the selected scan. The pose may be used to control image processing, such as filtering or reconstruction based on arm or leg position relative to the torso.

In one embodiment, the patient weight, height, or weight and height are used to control the scan. Rather than a nurse or physician estimating the weight of a patient (e.g., such as estimating during an emergency), the weight is estimated using the patient modeling. The intensity, spatial position of the scan, scan pattern, radiation dose, and/or image processing is configured based on the estimated weight. For example, without a weight—based adjustment, patients are exposed to a 17-43% higher radiation-dose from a chest computed tomography (CT) scan. The height may be used to configure the scan range.

In other embodiments, one or more internal body markers are used to control. The internal body markers may be used for simulating a topogram or image. The scanner is then configured to image based on the simulated results. In another example, the internal body markers are used to set the spatial position of the scan, such as the scan range.

The configured medical scanner scans the patient. For diagnosis, the patient is imaged. The imaging is performed based on the configuration of the medical scanner. For therapy, the therapeutic system applies the radiation or dose based on the configuration.

FIG. 6 shows one embodiment of a medical scanner system using patient modeling. The medical scanner system includes the display 60, memory 64, and image processor 62. The display 60, image processor 62, and memory 64 may be part of the medical scanner 66, a computer, server, workstation, or other system for image processing medical images from a scan of a patient. A workstation or computer without the medical scanner 66 may be used as the medical imaging system. The medical imaging system also includes the sensor 67 for sensing (imaging) an outer surface of a patient.

Additional, different, or fewer components may be provided. For example, a computer network is included for remote image generation of locally captured surface data or for local estimation of patient characteristics from remotely captured surface data. The machine-learned progressive multi-task model is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks). In yet another example, the medical scanner 66 is not provided.

The sensor 67 is a depth sensor or camera. LIDAR, 2.5D, RGBD, stereoscopic optical sensor, or other depth sensor may be used. A 2D camera may be used, such as using structure-from-motion. One sensor 67 is shown, but multiple sensors may be used. A light projector may be provided. The sensor 67 may directly measure depth from the sensor 67 to the patient. The sensor 67 may include a separate processor for determining depth measurements from images, or the image processor 62 determines the depth measurements from images captured by the sensor 67. The depth may be relative to the sensor 67 and/or a bed or table 69.

The sensor 67 is directed at the patient 68. The sensor 67 may be part of or connected to the medical scanner 66 or is separate from the medical scanner 66.

The sensor 67 is configured to measure depths to or for a patient. The depths are distances from the sensor 67, table 69, or other location to the patient at various locations on the patient. Any sample pattern over the patient may be used. The sensor 67 outputs depth measurements and/or a surface image.

The image processor 62 is a controller, control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing surface data. The image processor 62 is a single device, a plurality of devices, or a network of devices. For more than one device, parallel or sequential division of processing may be used. Different devices making up the image processor 62 may perform different functions, such as a processor for patient modeling and another processor (e.g., controller) for controlling scanning based on the patient modeling. In one embodiment, the image processor 62 is a control processor or other processor of the medical scanner 66. The image processor 62 operates pursuant to and is configured by stored instructions, hardware, and/or firmware to perform various acts described herein.

The image processor 62 or other remote processor is configured to train a machine learning architecture. Based on a user provided or other source of the network architecture and training data, the image processor 62 learns to relate one or more input variables (e.g., surface data) to outputs for different tasks in patient modeling. The training is progressive so that features learned for one or more networks are used as constants in training other networks. The result of the training is a machine-learned progressive multi-task network for patient modeling.

Alternatively or additionally, the image processor 62 is configured to apply the multi-task progressive machine-learned network. In response to input of surface data, part of the machine-learned model outputs a value or values for one or more characteristics. The output is based on values determined for features within the part. One or more of these feature values are used in other parts of the machine-learned model for generating outputs for other tasks (i.e., other characteristics of the patient).

In one embodiment, the image processor 62 is configured to determine two or more characteristics from the group of characteristics of patient pose, patient height, patient weight, patient interior landmark, and patient exterior landmark. The values of the characteristics are determined by application of the progressive multi-task machine-learned model to the surface data.

The image processor 62 may be a controller. The controller is configured by software, firmware, and/or hardware to operate the medical scanner 66 based on the patient pose, patient height, patient weight, and/or patient landmark. The multi-task progressive machine-learned model outputs information for multiple tasks. The outputs for the multiple tasks are used to configure the medical scanner 66 for scanning the patient 68.

The display 60 is a CRT, LCD, projector, plasma, printer, tablet, smart phone or other now known or later developed display device for displaying the output, such as an image of values of the characteristics, image from the sensor 67, and/or image from the medical scanner 66.

The sensor measurements, surface data, network definition, features, machine-learned model, feature values, and/or other information are stored in a non-transitory computer readable memory, such as the memory 64. The memory 64 is an external storage device, RAM, ROM, database, and/or a local memory (e.g., solid state drive or hard drive). The same or different non-transitory computer readable media may be used for the instructions and other data. The memory 64 may be implemented using a database management system (DBMS) and residing on a memory, such as a hard disk, RAM, or removable media. Alternatively, the memory 64 is internal to the processor 62 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 64). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical scanner 66 is a therapeutic radiation or diagnostic scanner, such as an x-ray or particle therapy system. The medical scanner 66 operates pursuant to one or more settings to apply scan a patient. The settings control scanning including transmission, reception, reconstruction, and image processing. One or more of the settings are set, at least in part, by values of characteristics output by the progressive multi-task machine-learned model. Once configured by the settings, the medical scanner 66 scans the patient.

In some embodiments, a medical scanner is configured to scan an internal region of a patient and generate diagnostic information from the scan. The medical scanner is a CT, MR, positron emission tomography (PET), single photon emission computed tomography (SPECT), X-ray, or ultrasound scanner. The medical scanner 66 may be configured to generate diagnostic image information. The configuration uses settings for one or more parameters, such as an X-ray source voltage, table position and/or range of movement, gantry position and/or range of movement, focus, field of view, scan density, detector thresholds, transmission sequence, image processing settings, filtering settings, reconstruction settings, and/or image generation settings. Based on the characteristic of the patient generated from the surface data, one or more settings of the medical scanner are automatically or manually set. The patient 68 is imaged by the medical scanner using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for patient modeling from surface data in a medical system, the method comprising:
    capturing, with a sensor, an outer surface of a patient, the surface data being from the capturing of the outer surface of the patient;
    estimating, by a processor, a first value of a first patient characteristic from the surface data as a first task, the first patient characteristic estimated by a first machine-learned model of a progressive multi-task network;
    estimating, by the processor, a second value of a second patient characteristic from the surface data as a second task, the second patient characteristic estimated by a second machine-learned model of the progressive multi-task network, the second machine-learned model including features learned in training the first machine-learned model, the second machine-learned model having been trained after the first machine-learned model using the features learned in training the first machine-learned model as unchanging in the training of the second machine-learned model; and
    controlling, by the processor, scanning by a medical scanner of the patient based on the first and second values of the first and second patient characteristics.

2. The method of claim 1 wherein capturing comprises capturing with the sensor being a depth sensor.

3. The method of claim 1 wherein capturing comprises capturing with the sensor being a camera where the surface data is based on optical measurements.

4. The method of claim 1 wherein the first characteristic is a different type of characteristic than the second characteristic, the first and second characteristics each being one of landmarks, pose, body shape, weight, height, or internal body markers.

5. The method of claim 1 wherein estimating the first value comprises estimating with the features being learned convolution kernels from within first machine-learned model, the first machine-learned model comprising a first image-to-image network.

6. The method of claim 5 wherein estimating the second value comprises estimating with the second machine-learned model comprising a second image-to-image network, the features being from an encoder of the first image-to-image network and being used in an encoder of the second image-to-image network.

7. The method of claim 5 wherein estimating the second value comprises estimating with the second machine-learned model comprising a neural network, the features being at a bottleneck of the first image-to-image network and being used as inputs to the neural network.

8. The method of claim 1 wherein estimating the first value comprises estimating with the first machine-learned model comprising a first encoder-decoder trained to output upper body landmarks as the first characteristic, wherein estimating the second value comprises estimating with the second machine-learned model comprises a second encoder-decoder trained to output lower body landmarks as the second characteristic, further comprising estimating a third value for a third characteristic as a third task by a third machine-learned model, the third machine-learned model having been trained after the first machine-learned models using the features learned in training the first machine-learned models as unchanging in the training of the third machine-learned model.

9. The method of claim 1 wherein the second machine-learned model was trained using the features learned in training the first machine-learned model as constants such that the features do not change in the training for estimating by the first machine-learned model.

10. The method of claim 1 wherein the second characteristic comprises body shape, and wherein controlling comprises setting an iso-center using the body shape.

11. The method of claim 1 wherein the first characteristic comprises one or more landmarks, and wherein controlling comprises setting a scan range using the one or more landmarks.

12. The method of claim 1 wherein the second characteristic comprises a patient pose, and wherein controlling comprises re-orienting the patient on a bed or correcting a pose entered into a medical scanner.

13. The method of claim 1 wherein the second characteristic comprises body shape, and wherein controlling comprises performing a magnetic resonance scan with specific absorption rate settings based on the body shape.

14. The method of claim 1 wherein the second characteristic comprises a patient weight, height, or weight and height, and wherein controlling comprises configuring a scan based on the weight, height, or weight and height.

15. The method of claim 1 wherein the second characteristic estimated by the second machine-learned model comprises an internal body marker, and wherein controlling comprises controlling based on a simulated topogram or image from the internal body marker.

16. The method of claim 1 wherein controlling comprises configuring the medical scanner comprising a medical diagnostic imaging scanner or therapeutic scanner to scan based on the first and second values.

17. A medical scanner system using patient modeling, the medical scanner system comprising:
    a depth camera configured to measure depths to a patient while the patient is on a patient bed in a medical scanner;
    an image processor configured to determine two or more of patient pose, patient height, patient weight, patient shape, and patient landmark by application of a progressive multi-task machine-learned model; and
    a controller configured to operate the medical scanner based on the patient pose, patient height, patient weight, and patient landmark.

18. The medical scanner system of claim 17 wherein the progressive multi-task machine-learned model comprises a neural network for each of the two or more of the patient pose, patient height, patient weight, and patient landmark, features learned from one of the neural networks being used in another one of the neural networks.

* * * * *